US007429471B2

(12) United States Patent
Brighton

(10) Patent No.: US 7,429,471 B2
(45) Date of Patent: *Sep. 30, 2008

(54) REGULATION OF MATRIX METALLOPROTEINASE GENE EXPRESSION USING SPECIFIC AND SELECTIVE ELECTRICAL AND ELECTROMAGNETIC SIGNALS

(75) Inventor: Carl T. Brighton, Malvern, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 164 days.

This patent is subject to a terminal disclaimer.

(21) Appl. No.: 10/461,188

(22) Filed: Jun. 13, 2003

(65) Prior Publication Data

US 2004/0138709 A1    Jul. 15, 2004

Related U.S. Application Data

(63) Continuation-in-part of application No. 10/257,126, filed as application No. PCT/US01/05991 on Feb. 23, 2001.

(60) Provisional application No. 60/184,491, filed on Feb. 23, 2000.

(51) Int. Cl.
*C12N 13/00* (2006.01)
(52) U.S. Cl. ...................... 435/173.8; 607/50
(58) Field of Classification Search ............... 435/375, 435/377, 173.8; 607/65
See application file for complete search history.

(56) References Cited

U.S. PATENT DOCUMENTS

| 4,430,999 | A | | 2/1984 | Brighton et al. ............ 128/419 |
|---|---|---|---|---|
| 4,442,846 | A | | 4/1984 | Brighton et al. ............ 128/784 |
| 4,467,808 | A | | 8/1984 | Brighton et al. .......... 128/419 F |
| 4,467,809 | A | * | 8/1984 | Brighton ..................... 607/51 |
| 4,487,834 | A | | 12/1984 | Brighton ..................... 435/173 |
| 4,506,674 | A | | 3/1985 | Brighton et al. ............ 128/419 |
| 4,509,520 | A | | 4/1985 | Dugot ........................ 128/419 |
| 4,535,775 | A | | 8/1985 | Brighton et al. .......... 128/419 F |
| 4,549,547 | A | | 10/1985 | Brighton et al. .......... 128/419 F |
| 4,600,010 | A | * | 7/1986 | Dugot .......................... 607/27 |
| 4,683,873 | A | | 8/1987 | Cadossi et al. .............. 128/1.5 |
| 4,998,532 | A | | 3/1991 | Griffith |
| 5,014,699 | A | | 5/1991 | Pollack et al. .............. 128/419 |
| 5,038,797 | A | | 8/1991 | Batters ....................... 128/798 |
| 5,269,746 | A | | 12/1993 | Jacobson .................... 600/13 |
| 5,273,033 | A | | 12/1993 | Hoffman .................... 607/46 |
| 5,338,286 | A | | 8/1994 | Abbott et al. ............... 600/14 |
| 5,374,283 | A | | 12/1994 | Flick .......................... 607/46 |
| 5,743,844 | A | | 4/1998 | Tepper et al. ............... 600/14 |
| 5,968,527 | A | | 10/1999 | Litovitz ...................... 424/400 |
| 6,083,149 | A | | 7/2000 | Wascher et al. ............. 600/9 |
| 6,132,362 | A | | 10/2000 | Tepper et al. ............... 600/14 |
| 6,186,940 | B1 | | 2/2001 | Kirschbaum .............. 600/12 |
| 6,261,221 | B1 | | 7/2001 | Tepper et al. ............... 600/14 |
| 6,292,699 | B1 | | 9/2001 | Simon et al. |
| 6,485,963 | B1 | | 11/2002 | Wolf et al. |
| 6,605,089 | B1 | | 8/2003 | Michelson .................. 606/61 |
| 6,747,004 | B1 | | 6/2004 | Tabibzadeh ................ 514/12 |
| 6,919,205 | B2 | | 7/2005 | Brighton |
| 6,955,642 | B1 | | 10/2005 | Simon |
| 7,022,506 | B2 | | 4/2006 | Brighton et al. |
| 7,130,692 | B2 | | 10/2006 | Brighton et al. |
| 7,158,835 | B2 | | 1/2007 | Brighton et al. |
| 7,167,753 | B2 | | 1/2007 | Brighton et al. |
| 7,215,995 | B2 | | 5/2007 | Brighton et al. |
| 2002/0052634 | A1 | | 5/2002 | March ........................ 607/50 |
| 2002/0125769 | A1 | | 9/2002 | Riley et al. |
| 2003/0211084 | A1 | | 11/2003 | Brighton et al. ........... 424/93.7 |
| 2004/0138709 | A1 | | 7/2004 | Brighton |
| 2005/0203591 | A1 | | 9/2005 | Brighton |
| 2006/0190043 | A1 | | 8/2006 | Brighton et al. |
| 2006/0235473 | A1 | | 10/2006 | Brighton |

(Continued)

FOREIGN PATENT DOCUMENTS

EP       1198580 B1    5/2006

(Continued)

OTHER PUBLICATIONS

Jiang et al., Journal of Cellular Physiology, vol. 202, 2005, pp. 723-730.*

(Continued)

*Primary Examiner*—James Ketter
(74) *Attorney, Agent, or Firm*—Woodcock Washburn LLP

(57) ABSTRACT

Methods and devices for the regulation of matrix metalloproteinase gene expression in cartilage cells via the application of fields generated by specific and selective electric and electromagnetic signals in the treatment of diseased or injured articular cartilage. By gene expression is meant the up-regulation or down-regulation of the process whereby specific portions (genes) of the human genome (DNA) are transcribed into mRNA and subsequently translated into protein. Methods and devices are provided for the targeted treatment of injured or diseased cartilage tissue that include generating specific and selective electric and electromagnetic signals that generate fields optimized for reduction of matrix metalloproteinase gene expression and exposing cartilage tissue to the fields generated by specific and selective signals so as to regulate matrix metalloproteinase gene expression in such cartilage tissue. The resulting methods and devices are useful for the targeted treatment of osteoarthritis, rheumatoid arthritis, cartilage injury, cartilage defects, and tumor metastasis.

24 Claims, 7 Drawing Sheets

U.S. PATENT DOCUMENTS

2007/0299472 A1   12/2007   Brighton

FOREIGN PATENT DOCUMENTS

| WO | WO 00/02585 A1 | 1/2000 |
| --- | --- | --- |
| WO | 01162336 A1 | 8/2001 |
| WO | WO 01/62336 A1 | 8/2001 |
| WO | 2005070136 A2 | 8/2005 |
| WO | WO 2005/070136 A2 | 8/2005 |

OTHER PUBLICATIONS

Ala-aho et al., Oncogene, vol. 23, 2004, pp. 5111-5123.*

Aaron, R.K., et al., "The conservative treatment of osteonecrosis of the femoral head," *Clin. Orthop.*, 1989, 249, 209-218.

Aaron, R.K., et al., "Stimulation of experimental endochondral ossification by low-energy pulsing electromagnetic fields," *J. Bone Miner. Res.*, Nov. 2, 1989, 4, 227-233.

Bassett,C.A.L., "Low energy pulsing electromagnetic fields modify biomedical processes," *BioEssays*, 1987, 6(1), 36-42.

Bassett, C.A.L., et al., "Effects of pulsed electromagnetic fields on Steinberg ratings of femoral head osteonecrosis," *Clin. Orthop.*, Sep. 1989, 246, 172-185.

Bassett, C.A.L., et al., "Fundamental and practical aspects of therapeutic uses of pulsed electromagnetic fields (PEMSs)," *Crit. Rev. Biomed. Eng.*, 1989, 17(5), 451-529.

Bassett, C.A.L., et al., "Pulsing electromagnetic field treatment in ununited fractures and failed arthrodeses," *JAMA*, Feb. 5, 1982, 247(5), 623-628.

Binder, A., et al., "Pulsed electromagnetic field therapy of persistent rotator cuff tendonitis," *Lancet*, Mar. 31, 1984, 695-698.

Brighton, C.T., et al., "A multicenter study of the treatment of nonunion with constant direct current," *J. Bone and Joint Surgery*, Jan. 1981, 63-A(1), 2-12.

Brighton, C.T., et al., "Treatment of recalcitrant non-union with a capacitively coupled electrical field," *J. Bone and Joint Surgery*, Apr. 1985, 67-A(4), 577-585.

Brighton, C.T., et al., "Treatment of castration-induced osteoporosis by a capacitively coupled electrical signal in rat vertebrae," *J. Bone and Joint Surgery*, Feb. 1989, 71-A(2), 228-236.

Brighton, C.T., "Increased cAMP production after short-term capacitively coupled stimulation in bovine growth plate chondrocytes," *J. Orthop. Res.*, 1988, 6, 552-558.

Brighton, C.T., et al., "Treatment of denervation/disuse osteoporosis in the rat with a capacitively coupled electrical signal: effects on bone formation and bone resporption," *J. Orthop. Res.*, 1988, 6, 676-684.

Goodman, R., et al., "Exposure of salivary gland cells to low-frequency electromagnetic fields alters polypeptide synthesis," *Proc. Natl. Acad. Sci. USA*, Jun. 1988, 85, 3928-3932.

Goodwin, C.B., et al., "A double-blind study of capacitively coupled electrical stimulation as an adjunct to lumbar spinal fusions," *Spine*, 1999, 24(13), 1349-1356.

Grodzinsky, A.J., "Electromechanical and physicochemical properties of connective tissue," *Crit. Rev. Biomed. Engng.*, 1983, 9(2), 133-199.

Harrison, M.H.M., et al., "Use of pulsed electromagnetic fields in perthes disease: report of a pilot study," *J. Pediatr. Orthop.*, 1984, 4, 579-584.

Jones, D.B., et al., "PEMF effects on differentiation and division in mirine melanoma cells are mediated indirectly through cAMP," *Trans. BRAGS 6*, 1986, 51.

Lorich, D.G., et al., "Biochemical pathway mediating the response of bone cells to capacitive coupling," *Clin. Orthop. and Related Res.*, 1998, 350, 246-256.

Massardo, L., et al., "Osteoarthritis of the knee joint: an eight year prospective study," *Ann Rheum Dis.*, 1989, 48, 893-897.

Mooney, V., "A randomized double-blind prospective study of the efficacy of pulsed electromagnetic fields for inter body lumbar fusions," *Spine*, 1990, 15(7), 708-712.

Brighton, C.T., et al., "Fracture healing in the rabbit fibula when subjected to various capacitively coupled electrical fields," *J. Orthop. Res.*, 1985, 3, 331-340.

Brighton, C.T., et al., "In vitro bone-cell response to a capacitively coupled electrical field," *Clin. Orthop. Related Res.*, Dec. 1992, 285, 255-262.

Carter, E.L., et al., "Fields distributions in vertebral bodies of the rat during electrical stimulation: a parametric study," *IEEE Trans. on Biomed. Eng.*, Mar 1989, 36(3), 333-345.

Brighton, C.T., et al., "Signal transduction in electrically stimulated bone cells," *J. Bone Joint Surg. Am.*, 2001, 83-A(10), 1514-1523.

Pienkowski, D., et al., "Low-power electromagnetic stimulation of osteotomized rabbit fibuiae," *J. of Bone & Joint Surgery*, 1994, 76-A(4), 489-501.

Wang, W., et al., "Up-regulation of chondrocyte matrix genes and products by electric fields," *Clin. Orthopaedics & Related Res.*, 2004, 427S, S163-S173.

Norton, L.A., et al., "Pulsed electromagnetic fields alter phenotypic expression in chondroblasts in tissue culture," *J. Orthop. Res.*, 1988, 6, 685-689.

Rodan, G.A., et al., "DNA synthesis in cartilage cells is stimulated by oscillating electric fields," *Science*, Feb. 10, 1978, 199, 690-692.

Ryaby, J.T., et al., "Pulsing electromagnetic fields affect the phosphorylation and expression of oncogene proteins," *Trans. BRAGS 6*, 1986, p. 78.

Ryaby, J.T., et al., "The effect of electromagnetic fields on protein phosphorylation and synthesis in murine melanoma cells," *BRAGS*, p. 32, (1986).

Wang, W., et al., "The increased level of PDGF-A constributes to the increased proliferation induced by mechanical stimulation in osteoblastic cells," *Biochem. And Molecular Biol. International*, Oct. 1997, 43(2), 339-346.

Zhuang, H., et al., "Mechanical strain-induced proliferation of osteoblastic cells parallels increased TGF-$\beta$1 mRNA,"*Biochem. Biophys. Res. Commun.*, 1996, 229, 449-453.

Zhuang, H., et al., "Electrical stimulation induces the level of TGF-$\beta$1 mRNA in osteoblastic cells by a mechanism involving calcium/calmodulin pathway," *Biochem. Biophys. Res. Commun.*, 1997, 237, 225-229.

Wang, W., et al., "The increased level of PDGF-A constributes to the increased proliferation induced by mechanical stimulation in osteoblastic cells," *Biochem. and Molecular Biiology International*, Oct. 1997, 43(2), 339-346.

Zhuang, H., et al., "Electrical stimulation induces the level of TGF-$\beta$1 mRNA in osteoblastic cells by a mechanism involving calcium/calmodulin pathway," *Biochem. and Biophys. Res. Commun.*, 1997, 237, 225-229.

Zhuang, H., et al., "Mechanical strain-induced proliferation of osteoblastic cells parallels increased TGF-$\beta$1 mRNA," *Biochem. and Biophys. Res. Commun.*, 1996, 229, 449-453.

Brighton, C.T., et al., "Prevention and treatment of sciatic denervation disuse osteoporosis in rat tibia with capacitively coupled electrical stimulation," *Bone*, 1985, 6, 87-97.

Brighton, C.T., et al., "Treatment of nonunion of the tibia with a capacitively coupled electrical field," *J. of Trauma*, 1984, 24(2), 153-155.

Brighton, C.T., et al., "Tibial nonunion treated with direct current, capacitive coupling, or bone graft," *Clin. of Orthop. and Related Res.*, 1995, 321, 223-234.

Heermeier, K., et al., "Effects of extremely low frequency electromagnetic field (EMF) on collagen type 1 mRNA expression and extracellular matrix synthesis of human osteoblastic cells," Bioelectromagnetics, 1998, 19(4), 222-231.

Pezzetti, F., et al., "Effects of pulsed electromagnetic fields on human chondrocytes: an in vitro study," Calcif Tissue Int., 1999, 65(5), 396-401.

* cited by examiner

REGULATION OF MATRIX METALLOPROTEINASE GENE EXPRESSION USING SPECIFIC AND SELECTIVE ELECTRICAL AND ELECTROMAGNETIC SIGNALS

CROSS-REFERENCE TO RELATED APPLICATIONS

The present patent application is a continuation-in-part patent application of U.S. patent application Ser. No. 10/257,126, filed Oct. 8, 2002, which is the U.S. national phase patent application of PCT/US01/05991, filed Feb. 23, 2001, which, in turn, claims the benefit of the filing date of U.S. Provisional Patent Application Ser. No. 60/184,491, filed Feb. 23, 2000.

FIELD OF THE INVENTION

The present invention is directed to a method of down-regulating matrix metalloproteinase (MMP) gene expression in cartilage cells via the application of fields generated by specific and selective electric and electromagnetic signals for the treatment of injured or diseased articular cartilage, as well as devices for generating such signals.

BACKGROUND OF THE INVENTION

The bioelectrical interactions and activity believed to be present in a variety of biological tissues and cells are one of the least understood of the physiological processes. However, there has recently been much research into these interactions and activity regarding the growth and repair of certain tissues and cells. In particular, there has been much research into stimulation by electric and electromagnetic fields and its effect on the growth and repair of bone and cartilage. Researchers believe that such research might be useful in the development of new treatments for a variety of medical problems.

Osteoarthritis, also known as degenerative joint disease, is characterized by degeneration of articular cartilage as well as proliferation and remodeling of subchondral bone. The usual symptoms are stiffness, limitation of motion, and pain. Osteoarthritis is the most common form of arthritis, and prevalence rates increase markedly with age. It has been shown that elderly patients with self-reported osteoarthritis visit doctors twice as frequently as their unaffected peers. Such patients also experience more days of restricted activity and bed confinement compared to others in their age group. In one study, the majority of symptomatic patients became significantly disabled during an 8-year follow-up period (Massardo et al., *Ann. Rheum. Dis.* 48: 893-897, 1989).

Nonsteroidal anti-inflammatory drugs (NSAIDs) remain the primary treatment modality for osteoarthritis. It is unknown whether the efficacy of NSAIDs is dependent upon their analgesic or anti-inflammatory properties, or the slowing of degenerative processes in the cartilage. There is also a concern that NSAIDs may be deleterious to patients. For example, NSAIDs have well known toxic effects in the stomach, gastrointestinal tract, liver and kidney. However, aspirin inhibits proteoglycan synthesis and normal cartilaginous repair processes in animals. One study in humans suggested that indomethacin might accelerate breakdown of hip cartilage. All adverse effects appear more commonly in the elderly—the very population most susceptible to osteoarthritis.

In the disease commonly known as osteoporosis, bone demineralizes and becomes abnormally rarefied. Bone comprises an organic component of cells and matrix as well as an inorganic or mineral component. The cells and matrix comprise a framework of collagenous fibers that is impregnated with the mineral component of calcium phosphate (85%) and calcium carbonate (10%) that imparts rigidity to the bone. While osteoporosis is generally thought as afflicting the elderly, certain types of osteoporosis may affect persons of all ages whose bones are not subject to functional stress. In such cases, patients may experience a significant loss of cortical and cancellous bone during prolonged periods of immobilization. Elderly patients are known to experience bone loss due to disuse when immobilized after fracture of a bone, which may ultimately lead to a secondary fracture in an already osteoporotic skeleton. Diminished bone density may lead to vertebrae collapse, fractures of hips, lower arms, wrists, ankles as well as incapacitating pains. Alternative nonsurgical therapies for such diseases are needed.

Pulsed electromagnetic fields (PEMF) and capacitive coupling (CC) have been used widely to treat nonhealing fractures and related problems in bone healing since approval by the Food and Drug Administration in 1979. The original basis for the trial of this form of therapy was the observation that physical stress on bone causes the appearance of tiny electric currents that, along with mechanical strain, were thought to be the mechanisms underlying transduction of the physical stresses into a signal that promotes bone formation. Along with direct electric field stimulation that was successful in the treatment of nonunion, noninvasive technologies using PEMF and capacitive coupling (where the electrodes are placed on the skin in the treatment zone) were also found to be effective. Pulsed electromagnetic fields generate small induced currents (Faraday currents) in the highly-conductive extracellular fluid, while capacitive coupling directly causes currents in the tissues; both PEMFs and CC thereby mimic endogenous electrical currents.

The endogeneous electrical currents, originally thought to be due to phenomena occurring at the surface of crystals in the bone, have been shown to be due primarily to movement of fluid containing electrolytes in channels of the bone containing organic constituents with fixed negative charges, generating what are called "streaming potentials." Studies of electrical phenomena in cartilage have demonstrated a mechanical-electrical transduction mechanism that resembles those described in bone, appearing when cartilage is mechanically compressed, causing movement of fluid and electrolytes over the surface of fixed negative charges in the proteoglycans and collagen in the cartilage matrix. These streaming potentials apparently serve a purpose in cartilage similar to that in bone, and, along with mechanical strain, lead to signal transduction that is capable of stimulating chondrocyte synthesis of matrix components.

The main application of direct current, capacitive coupling, and PEMFs has been in orthopedics in healing of nonunion bone fractures (Brighton et al., *J. Bone Joint Surg.* 63: 2-13, 1981; Brighton and Pollack, *J. Bone Joint Surg.* 67: 577-585, 1985; Bassett et al., *Crit. Rev. Biomed. Eng.* 17: 451-529, 1989; Bassett et al., *JAMA* 247: 623-628, 1982). Clinical responses have been reported in avascular necrosis of hips in adults and Legg-Perthes's disease in children (Bassett et al., *Clin. Orthop.* 246: 172-176, 1989; Aaron et al., *Clin. Orthop.* 249: 209-218, 1989; Harrison et al., *J. Pediatr. Orthop.* 4: 579-584, 1984). It has also been shown that PEMFs (Mooney, *Spine* 15: 708-712, 1990) and capacitive coupling (Goodwin, Brighton et al., *Spine* 24: 1349-1356, 1999) can significantly increase the success rate of lumbar fusions. There are also reports of augmentation of peripheral nerve regeneration and function and promotion of angiogenesis (Bassett, *Bioessays* 6: 36-42, 1987). Patients with persistent rotator cuff tendonitis refractory to steroid injection and other conventional measures, showed significant benefit compared with placebo treated patients (Binder et al., *Lancet* 695-698, 1984). Finally, Brighton et al. have shown in rats the ability of an appropriate capacitive coupling electric field to both prevent and reverse vertebral osteoporosis in the lumbar spine (Brighton et al., *J. Orthop. Res.* 6: 676-684, 1988; Brighton et al., *J. Bone Joint Surg.* 71: 228-236, 1989).

More recently, research in this area has focused on the effects stimulation has on tissues and cells. For example, it has been conjectured that direct currents do not penetrate cellular membranes and that control is achieved via extracellular matrix differentiation (Grodzinsky, *Crit. Rev. Biomed. Eng.* 9:133-199, 1983). In contrast to direct currents, it has been reported that PEMFs can penetrate cell membranes and either stimulate them or directly affect intracellular organelles. An examination of the effect of PEMFs on extracellular matrices and in vivo endochondral ossification found increased synthesis of cartilage molecules and maturation of bone trabeculae (Aaron et al., *J. Bone Miner. Res.* 4: 227-233, 1989). More recently, Lorich, Brighton et al. reported (*Clin. Orthop. Related Res.* 350: 246-256, 1998) that signal transduction of a capacitively coupled electric signal is via voltage gated calcium channels, leading to an increase in cytosolic calcium with a subsequent increase in activated (cytoskeletal) calmodulin.

Much research has been directed at studying tissue culture in order to understand the mechanisms of response. In one study, it was found that electric fields increased [$^3$H]-thymidine incorporation into the DNA of chondrocytes, supporting the notion that $Na^+$ and $Ca^{2+}$ fluxes generated by electrical stimulation trigger DNA synthesis (Rodan et al., *Science* 199: 690-692, 1978). Studies have found changes in the second messenger, cAMP, and cytoskeletal rearrangements due to electrical perturbations (Ryaby et al., *Trans. BRAGS* 6: 1986; Jones et al., *Trans. BRAGS* 6: 51, 1986; Brighton and Townsend, *J. Orthop. Res.* 6: 552-558, 1988). Other studies have found effects on glycosamino-glycan, sulfation, hyaluronic acid, lysozyme activity and polypeptide sequences (Norton et al., *J. Orthop. Res.* 6: 685-689, 1988; Goodman et al., *Proc. Natl. Acad. Sci.* USA 85: 3928-3932, 1988).

It was reported in 1996 by the present inventors that a cyclic biaxial 0.17% mechanical strain produces a significant increase in TGF-$\beta_1$ mRNA in cultured MC3T3-E1 bone cells (Brighton et al., *Biochem. Biophys. Res. Commun.* 229: 449-453, 1996). Several significant studies followed in 1997. In one study it was reported that the same cyclic biaxial 0.17% mechanical strain produced a significant increase in PDGF-A mRNA in similar bone cells (Brighton et al., *Biochem. Biophys. Res. Commun.* 43: 339-346, 1997). It was also reported that a 60 kHz capacitively coupled electric field of 20 mV/cm produced a significant increase in TGF-$\beta_1$ in similar bone cells (Brighton et al., *Biochem. Biophys. Res. Commun.* 237: 225-229, 1997). However, the effect such a field would have on other genes has not been reported in the literature.

In the above-referenced parent patent application, entitled "Regulation of Genes Via Application of Specific and Selective Electrical and Electromagnetic Signals," methods were disclosed for determining the specific and selective electrical and electromagnetic signals for use in creating fields for regulating target genes of diseased or injured tissues. The present invention builds upon the technique described therein by describing the method of regulating one targeted gene expression, namely, matrix metalloproteinase gene expression, through application of a field generated by a specific and selective electrical and electromagnetic signal, for the treatment of cartilage disease (arthritis), cartilage injury, cartilage defects, and tumor metastasis.

SUMMARY OF THE INVENTION

The present invention relates to regulating the matrix metalloproteinase (MMP) gene expression in cartilage cells via the application of fields generated by specific and selective electric and/or electromagnetic signals. By performing dose-response curves on the electric field duration, amplitude, frequency, and duty cycle, the optimal signal for down-regulating matrix metalloproteinase mRNA in articular cartilage chondrocytes was discovered. The optimal signal generated a capacitively coupled electric field with an amplitude of 20 mV/cm, a duration of 30 minutes, a duty cycle of 100%, a frequency of 60 kHz, and a sine wave configuration. In particular, the present invention relates to down-regulating matrix metalloproteinase (MMP) gene expression in cartilage cells via the application of fields generated by such signals.

In a preferred embodiment of the invention, methods are provided to specifically and selectively down-regulate the gene expression (as measured by mRNA) of MMP-1, MMP-3 and MMP-13 and other MMPs, with capacitively coupled electric fields, inductively coupled electric fields, electromagnetic fields, or combined fields. Osteoarthritis, rheumatoid arthritis, cartilage injury, cartilage defects, and the like are treated with a capacitively or inductively coupled electric field of about 20 mV/cm with an electric field duration of about 30 minutes, an electric field amplitude of about 10-20 mV/cm, a frequency of about 60 kHz, a duty cycle of about, 100%, and a sine wave configuration that causes the expression of MMP-1, MMP-3 and MMP-13 mRNAs to be down-regulated. In accordance with the method of the invention, a "specific and selective" signal is a signal that has predetermined characteristics of amplitude, duration, duty-cycle, frequency, and waveform that down-regulates the expression of the MMP genes (specificity). This allows one to choose different signals to down-regulate MMP gene expressions in order to achieve a given biological or therapeutic response (selectivity). The invention further relates to devices employing the methods described herein to generate specific and selective signals that create fields to down-regulate the expression of MMP genes.

In related aspects, the present invention relates to methods and devices for the treatment of osteoarthritis, rheumatoid arthritis, cartilage injury, and cartilage defects. The method of the invention also includes the methodology for determining the "specific and selective" signal for MMP gene expression by methodically varying the duration of a starting signal known to decrease, or suspected to decrease, cellular production of metalloproteinases. After selecting the optimal duration, the amplitude of the signal is varied for the optimal duration of time as determined by the gene expression of MMP-1, MMP-3, MMP-13. The duty cycle, frequency, and waveform are varied methodically while keeping the other signal characteristics constant. This process is repeated until the optimal signal is determined that produces the greatest decrease in the expression of metalloproteinases.

These and other aspects of the present invention will be elucidated in the following detailed description of the invention.

DETAILED DESCRIPTION OF PREFERRED EMBODIMENTS OF THE INVENTION

Figure 1:
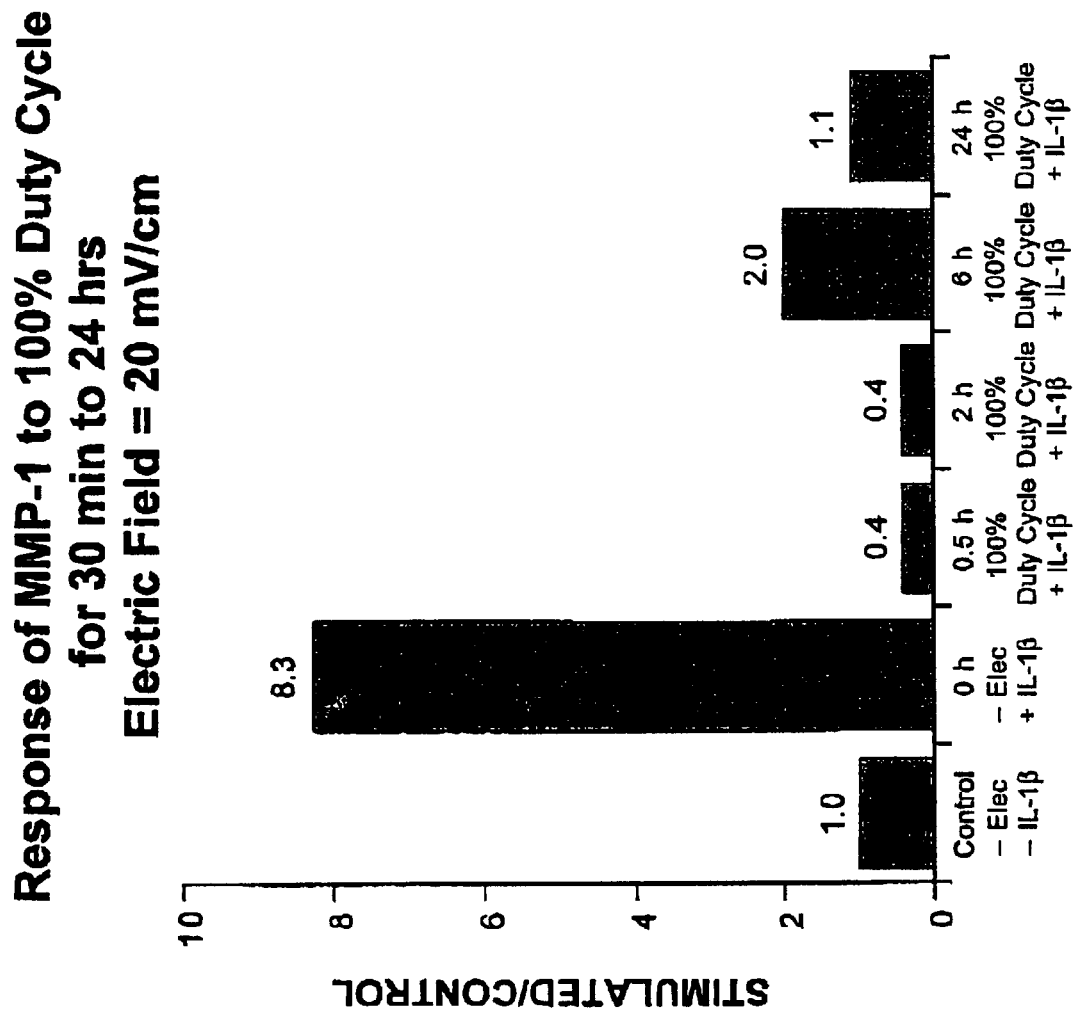
FIG. 1 is a graphic representation of MMP-1 mRNA expression when articular cartilage chondrocytes are exposed to a 20 mV/cm capacitively coupled electric field for various time durations in the presence of interleukin (IL-1β). As indicated, the minimum MMP-1 expression occurred when a signal was applied for 30 minutes. Maximum expression of MMP-1 mRNA occurred in the presence of IL-1β when no electricity was used.

The invention will be described in detail below with reference to FIGS. 1-7. Those skilled in the art will appreciate that the description given herein with respect to those figures is for exemplary purposes only and is not intended in any way to limit the scope of the invention. All questions regarding the scope of the invention may be resolved by referring to the appended claims.

The present invention is based on the discovery that the expression of certain genes can be regulated by the application of specific and selective fields generated by specific and selective electric and/or electromagnetic signals. In other words, it has been discovered by the present inventor that there is a specific electric and/or electromagnetic signal that generates a field for regulating each gene in bone, cartilage and other tissue cells and that these specific signals are capable of specifically and selectively regulating the genes in such cells. In particular, gene expression governing the growth, maintenance, repair, and degeneration or deterioration of tissues or cells can be regulated in accordance with the invention via the application of fields generated by specific and selective electric and/or electromagnetic signals so as to produce a salutary clinical effect. Such discoveries are useful in the development of treatment methods that target certain medical conditions including bone fractures and defects, osteoarthritis, osteoporosis, cancer and other diseases, as well as for developing devices employing such methods.

In particular, the present invention demonstrates that the expression of MMP may be significantly down-regulated to decrease the production of MMP in articular cartilage as is desired to slow or reverse the course of cartilage diseases. The present invention clearly shows that the optimal electric field described herein can significantly down-regulate MMP and, therefore, decrease MMP synthesis, even in the presence of IL-1β. Those skilled in the art will also appreciate that an appropriate electric field, as described herein with capacitive coupling but equally effective with inductive coupling and other known field application techniques, can be used to treat arthritis (both osteoarthritis and rheumatoid arthritis), cartilage injury, cartilage defects, and tissue cancers.

As used herein, the phrase "signal" is used to refer to a variety of signals including mechanical signals, ultrasound signals, electromagnetic signals and electric signals output by a device. It is to be understood that the term "field" as used herein refers to an electrical field within targeted tissue, whether it is a combined field or a pulsed electromagnetic field or generated by direct current, capacitive coupling or inductive coupling.

The phrase "remote" is used to mean acting, acted on or controlled from a distance. "Remote" regulation refers to controlling the expression of a gene from a distance. To provide "remotely" refers to providing from a distance. For example, providing a specific and selective signal from a remote source can refer to providing the signal from a source at a distance from a tissue or a cell, or from a source outside of or external to the body.

The phrase "specific and selective" signal means a signal that produces an electric field that has predetermined characteristics of amplitude, duration, duty cycle, frequency, and waveform that up-regulate or down-regulate a targeted gene or targeted functionally of complementary genes (specificity) . This allows one to choose different "specific and selective" signals to up-regulate or down-regulate expression of various genes in order to achieve a given biological or therapeutic response (selectivity).

The term "regulate" means to control gene expression. Regulate is understood to include both up-regulate and down-regulate. Up-regulate means to increase expression of a gene, while down-regulate means to inhibit or prevent expression of a gene.

"Functionally complementary" refers to two or more genes whose expressions are complementary or synergistic in a given cell or tissue.

"Tissue" refers to an aggregate of cells together with their extracellular substances that form one of the structural materials of a patient. As used herein, the term "tissue" is intended to include muscle and organ tissue, tumor tissue as well as bone or cartilage tissue. Also, the term "tissue" as used herein may also refer to an individual cell.

"Patient" refers to an animal, preferably a mammal, more preferably a human.

The present invention provides treatment methods and devices that target certain tissues, cells or diseases. In particular, the gene expression associated with the repair process in injured or diseased tissues or cells can be regulated by the application of fields generated by electric signals that are specific and selective for the genes to be regulated in the target tissues or cells. Gene expression can be up-regulated or down-regulated by the application of signals that are specific and selective for each gene or each set of complementary genes so as to produce a beneficial clinical effect. For example, a particular specific and selective signal may create an electric field that up-regulates a certain desirable gene expression, while the same or another particular specific and selective signal may create an electric field that down-regulates a certain undesirable gene expression. A certain gene may be up-regulated by a field generated by one particular specific and selective signal and down-regulated by a field generated by another specific and selective signal. Those skilled in the art will understand that certain diseased or injured tissues can be targeted for treatment by regulating those genes governing the growth, maintenance, repair, and degeneration or deterioration of the tissues.

The methods and devices of the present invention are based on identifying those signals that generate fields that are specific and selective for the gene expression associated with certain targeted diseased or injured tissue. For example, electricity in its various forms (e.g., capacitive coupling, inductive coupling, combined fields) can specifically and selectively regulate gene expression in targeted tissues or cells in a patient's body by varying the frequency, amplitude, waveform or duty cycle of the applied field for each selected gene. The duration of time exposed to electricity can also influence the capability of electricity to specifically and selectivity regulate gene expression in targeted tissues or cells in a patient's body. Specific and selective signals may generate electric fields for application to each gene systematically until the proper combination of frequency, amplitude, waveform, duty cycle, and duration is found that provides the desired effect on gene expression.

It is to be understood that a variety of diseased or injured tissues or disease states can be targeted for treatment because the specificity and selectivity of an electric field for a certain gene expression can be influenced by several factors. In particular, an electrical field of appropriate frequency, amplitude, waveform and/or duty cycle can be specific and selective for the expression of certain genes and thus provide for targeted treatments. Temporal factors (e.g., duration of time exposed to the electrical field) can also influence the specificity and selectivity of an electric field for a particular gene expression. The regulation of gene expression may be more effective (or made possible) via the application of an electrical field for a particular duration of time. Therefore, those skilled in the art will understand that the present invention provides for varying the frequency, amplitude, waveform, duty cycle and/or duration of application of an electric field until the electric field is found to be specific and selective for certain gene expressions in order to provide for treatments targeting a variety of diseased or injured tissue or diseases.

Thus, the present invention can provide for targeted treatments because it is possible to regulate expression of certain genes associated with a particular diseased or injured tissue via the application of fields generated by specific and selective signals of appropriate frequency, amplitude, waveform and/or duty cycle for an appropriate duration of time. The specificity and selectivity of a signal generating an electrical field may thus be influenced so as to regulate the expression of certain genes in order to target certain diseased or injured tissue or disease states for treatment. In particular, the present invention provides for the targeted treatment of osteoarthritis, rheumatoid arthritis, cartilage injury, and cartilage defects and metastases.

The present invention also provides devices that include a source of at least one signal specific and selective for down-regulation of matrix metalloproteinase gene expression. The devices of the present invention can provide for the production of such signals for application to cartilage cells by at least one electrode adapted to apply the field generated by the specific and selective signal in the case of capacitive coupling, and by extended coil(s) adapted to apply the field generated by the specific and selective signal in the use of inductive coupling. The optimal field described herein can be applied to any joint via appropriate surface electrodes, in pairs or strips, that are applied to the skin, incorporated in garments, braces, wraps or casts, and delivered by means of capacitive coupling, inductive coupling (electromagnetic fields), or combined fields.

Figure 7:
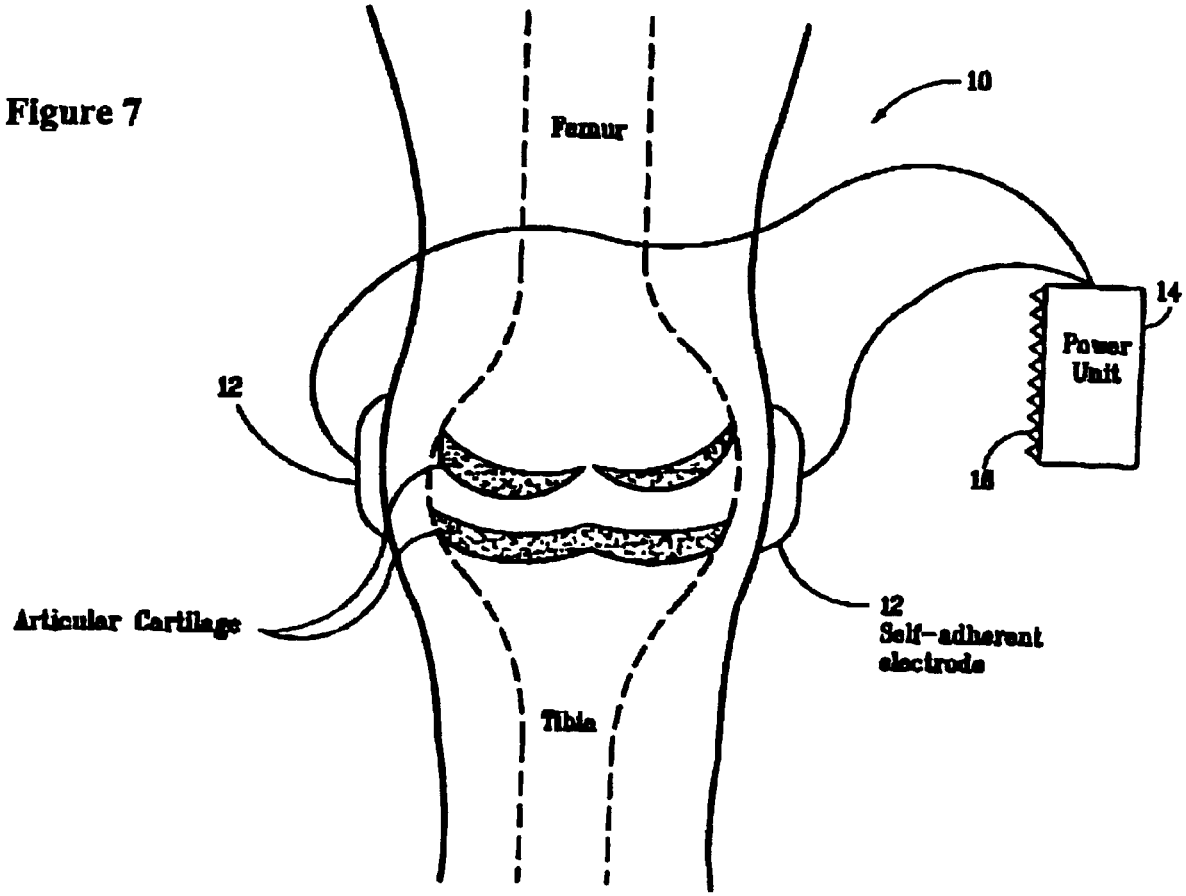
FIG. 7 is a diagram illustrating two different devices for the treatment of osteoarthritis of the knee, in accordance with preferred embodiments of the present invention.

The devices of the present invention are capable of applying a field generated by specific and selective signals directly to diseased or injured tissue and/or to the skin of a patient. The devices of the present invention may also provide for the remote application of specific and selective fields (e.g., application of a field at a distance from diseased or injured tissue), although it will be appreciated that capacitively coupled devices must touch the subject's skin. The devices of the present invention may include means for attaching the electrodes to the body of a patient in the vicinity of injured or diseased tissue in the case of capacitive coupling. For example, self-adherent conductive electrodes may be attached to the skin of the patient on both sides of a knee joint afflicted with osteoarthritis as shown in FIG. 7. As also shown in FIG. 7, the device 10 of the present invention may include self-adherent electrodes 12 for attaching the device 10 to the body of a patient. For example, the device 10 of the present invention may include electrodes 12 attached to a power unit 14 that has a VELCRO® patch 16 on the reverse side such that the power unit 14 can be attached to a VELCRO® strap (not shown) fitted around the calf, thigh or waist of the patient. In the case of inductive coupling, the device 10 of the present invention may include coils (not shown) attached to power unit 14 in place of electrodes 12.

The device 10 of the present invention can be employed in a variety of ways. The device 10 may be portable or may be temporarily or permanently attached to a patient's body. The device 10 of the present invention is preferably non-invasive. For example, the device 10 of the present invention may be applied to the skin of a patient by application of electrodes adapted for contact with the skin of a patient for the application of fields generated by the predetermined specific and selective signals. Such signals may also be applied via coils in which time-varying currents flow, thus producing specific and selective electromagnetic fields that penetrate the tissue. The device 10 of the present invention may also be capable of implantation in a patient, including implantation under the skin of a patient.

The example below will illustrate that the method of the present invention may provide for cartilage growth and repair. Cartilage growth and repair can be stimulated via signals specific and selective for the down-regulation of expression of matrix metalloproteinases in cartilage cells so as to prevent or inhibit articular cartilage destruction or deterioration in osteoarthritis patients. In particular, the methods of the present invention can provide for the down-regulation of matrix metalloproteinase genes that destroy cartilage. A variety of cartilage cells can be targeted by the methods of the present invention including articular chondrocytes and including articular cartilage, hyaline cartilage, and growth plate cartilage.

Those skilled in the art will understand that a variety of other cartilage diseases and injuries may be targeted for treatment via the method of the present invention.

Those skilled in the art will further understand that the devices of the present invention can be provided in a variety of forms including a capacitively coupled power unit with programmed, multiple, switchable, specific and selective signals for application to one pair or to multiple pairs of electrodes, or electromagnetic coils attached to a power unit with switchable, multiple, specific and selective signals, and an ultrasound stimulator with a power supply for generating specific and selective signals. Generally speaking, device preference is based on patient acceptance and patient compliance. The smallest and most portable unit available in the art at the present time is a capacitive coupling unit; however, patients with extremely sensitive skin may prefer to use inductive coupling units. On the other hand, ultrasound units require the most patient cooperation, but may be desirable for use by certain patients.

EXAMPLE

The invention is demonstrated in the following example, which is for purposes of illustration and is not intended to limit the scope of the present invention.

Materials and Methods

Chondrocyte cultures were prepared from either fetal or adult bovine articular cartilage. Chondrocytes ($5 \times 10^5$ cells/$cm^2$) were plated onto specially-modified Cooper dishes. The cells were grown to seven days with the medium changed just prior to beginning of the experimental condition. The experimental cell cultures throughout these studies were subjected to a capacitively coupled 60 kHz sine wave signal electric field with an output of 44.81 V peak-to-peak. This produced a calculated-field strength in the culture medium in the dishes of 20 mV/cm with a current density of 300 $\mu A/cm^2$. Control cell culture dishes were identical to that of the stimulated dishes except that the electrodes were not connected to a function generator.

Total RNA was isolated using TRIzol, according to the manufacturer's instructions, and reversed transcription (RT) using SuperScript II reverse transcriptase was performed. Oligonucleotide primers to be used in the RT-PCR technique were selected from published cDNA sequences or designed using the Primer Express software program. Quantitative real-time analysis of RT-PCR products was performed using an ABI Prism® 7000 Sequence Detection System.

Figure 2:
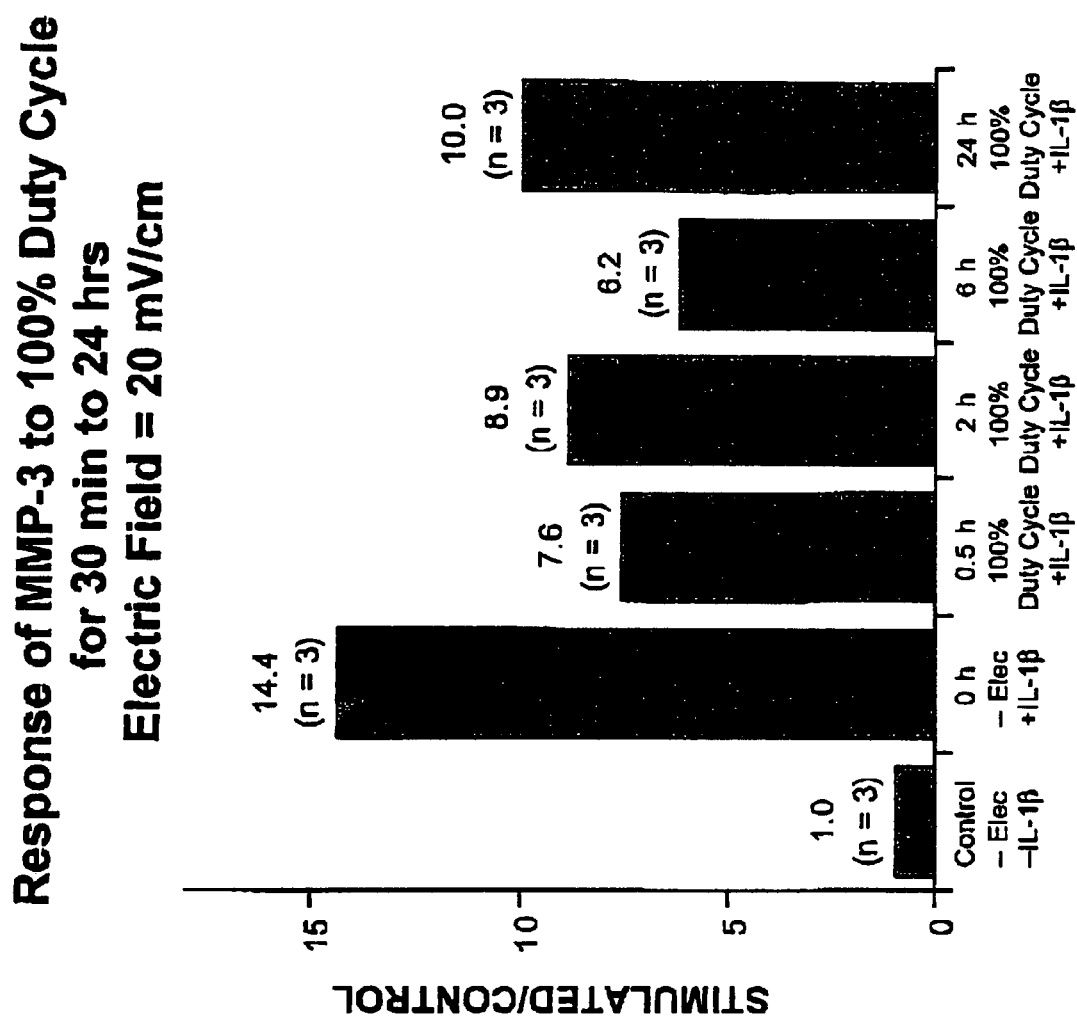
FIG. 2 is a graphic representation of MMP-3 mRNA expression when articular cartilage chondrocytes are exposed to a 20 mV/cm capacitively coupled electric field for various time durations in the presence of IL-1β. As indicated, the minimum MMP-3 expression occurred for signal durations of 30 minutes and 6 hours. Maximum expression of MMP-3 mRNA occurred in the presence of IL-1β when no electricity was used.
Figure 3:
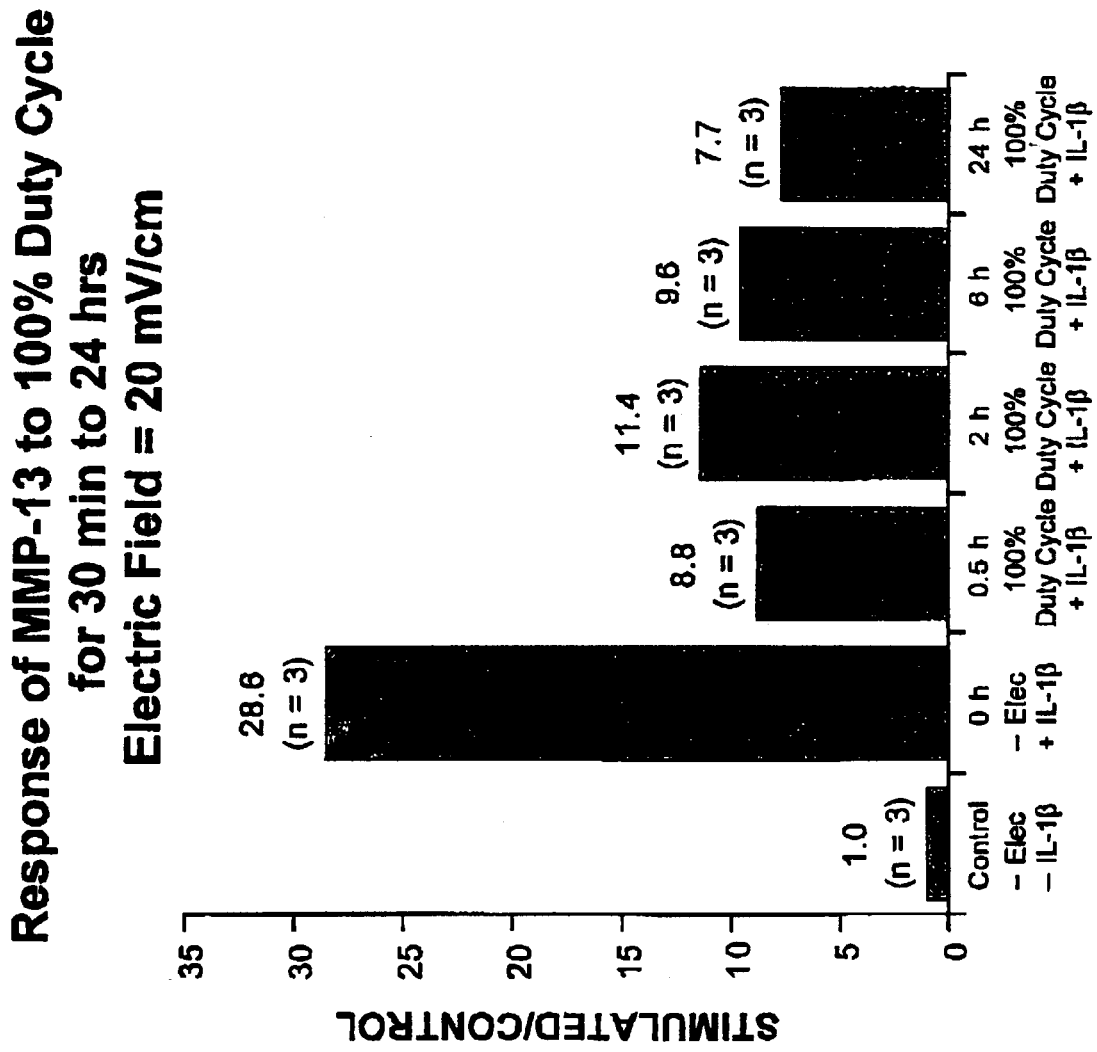
FIG. 3 is a graphic representation of MMP-13 mRNA expression when articular cartilage chondrocytes are exposed to a 20 mV/cm capacitively coupled electric field for various time durations in the presence of IL-1β. As indicated, the minimum MMP-13 expression occurred with signal durations of 30 minutes and 24 hours. Maximum expression of MMP-13 mRNA occurred in the presence of IL-1β when no electricity was used.
Figure 4:
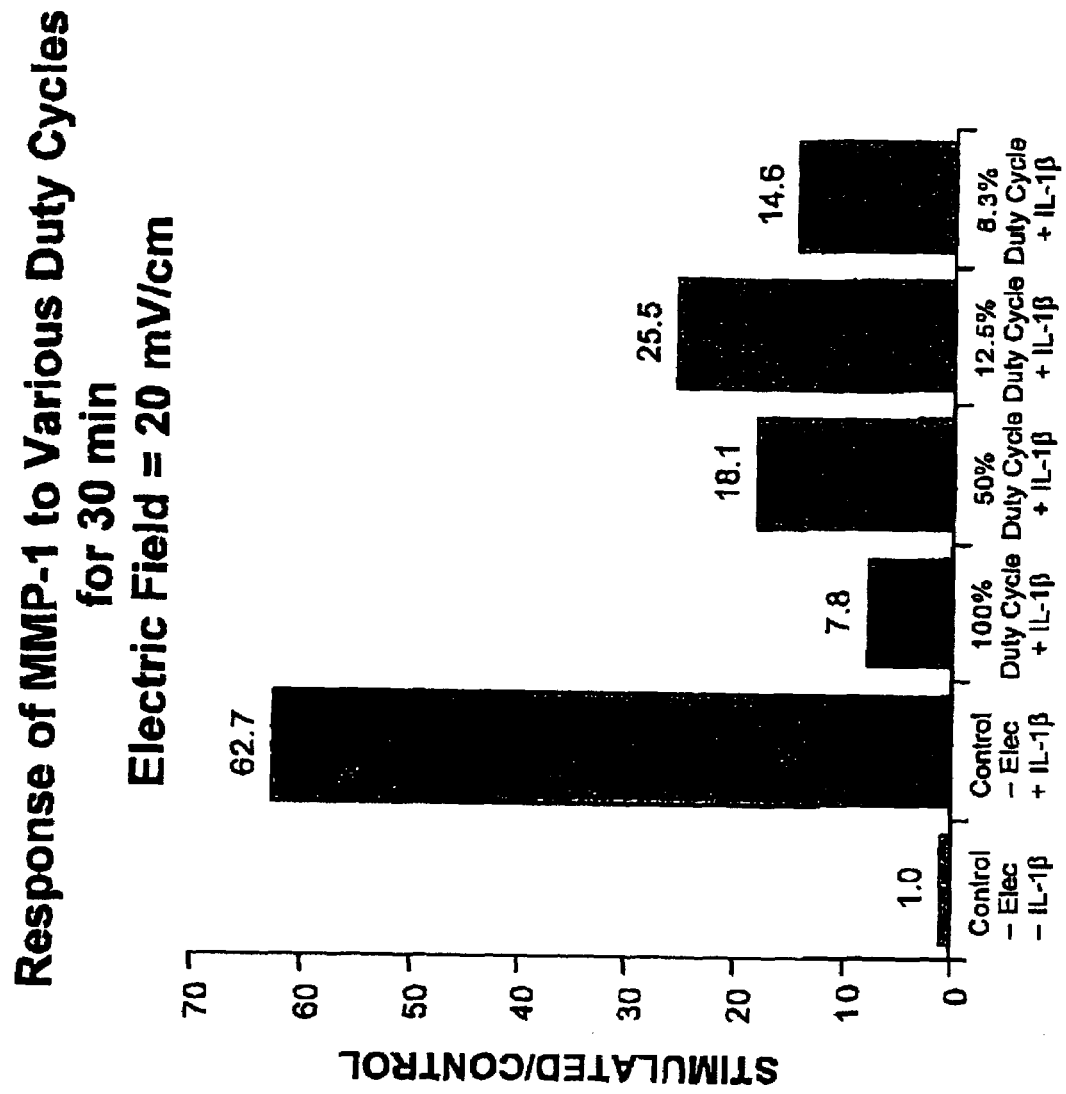
FIG. 4 is a graphic representation of MMP-1 mRNA expression when articular cartilage chondrocytes are exposed to a 20 mV/cm capacitively coupled electric field of different duty cycles in the presence of IL-1β. As indicated, the minimum expression of MMP mRNA occurred with a 100% duty cycle signal. Maximum expression of MMP-1 mRNA occurred in the presence of IL-1β when no electricity was used.
Figure 5:
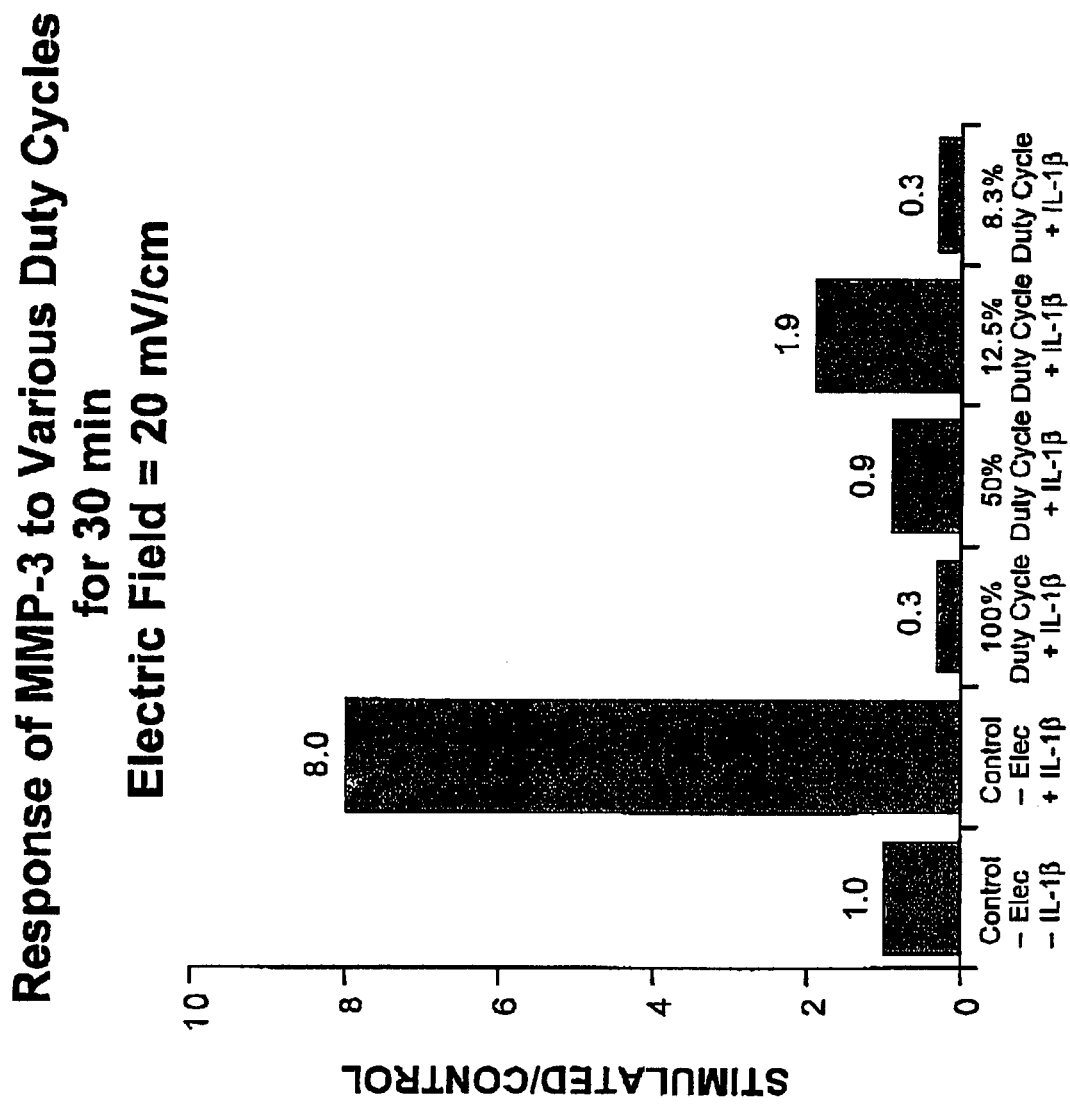
FIG. 5 is a graphic representation of MMP-3 mRNA expression when articular cartilage chondrocytes are exposed to a 20 mV/cm capacitively coupled electric field of different duty cycles in the presence of IL-1β. As indicated, minimum expressions occurred with 100% and 8.3% duty cycles. Maximum expression of MMP-3 mRNA occurred in the presence of IL-1β when no electricity was used.
Figure 6:
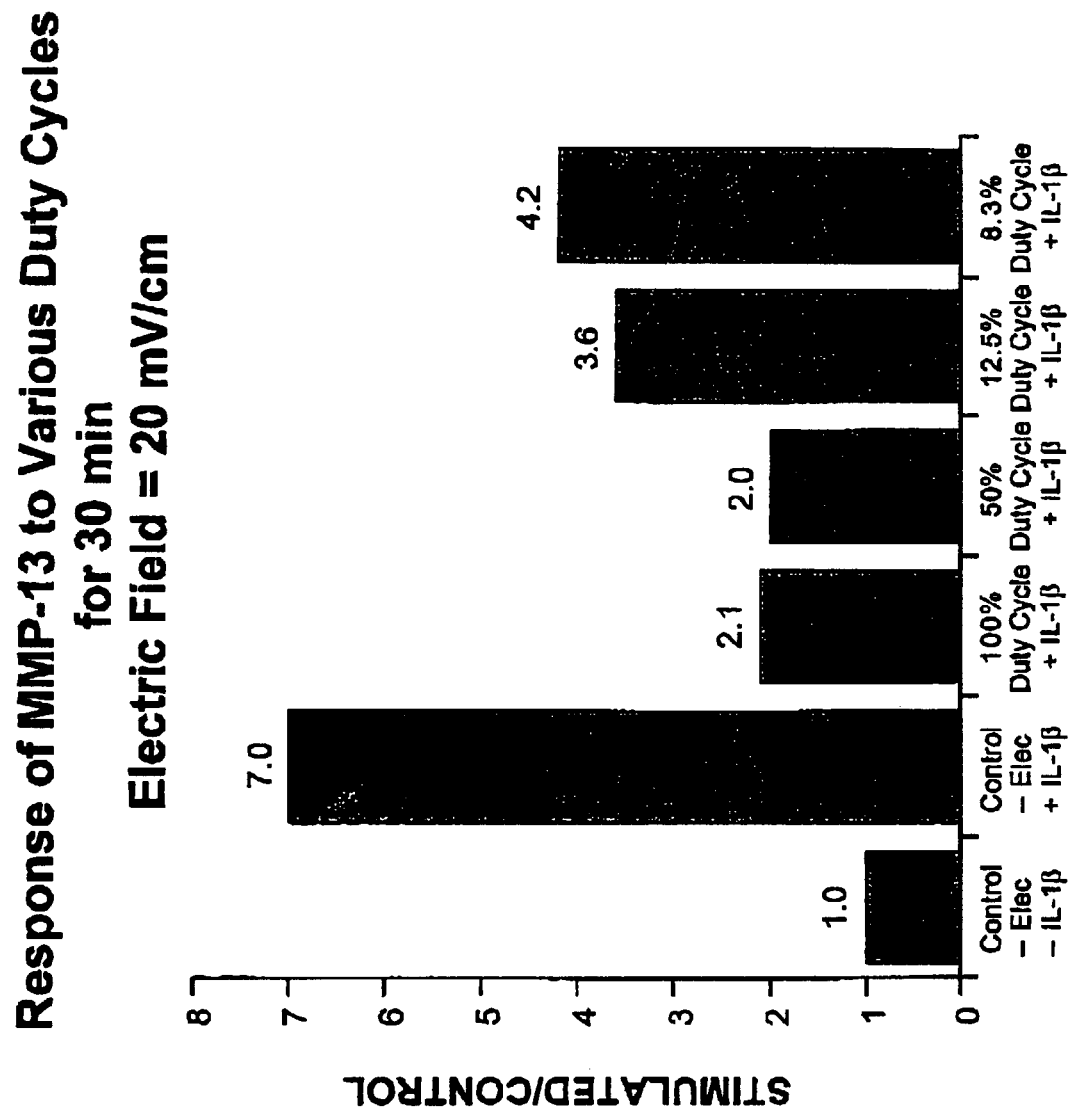
FIG. 6 is a graphic representation of MMP-13 mRNA expression when articular cartilage chondrocytes are exposed to a 20 mV/cm capacitively coupled electric field of different duty cycles in the presence of IL-1β. As indicated, minimum expressions occurred with duty cycles of 100% and 50%. Maximum expression of MMP-13 mRNA occurred in the presence of IL-1β when no electricity was used.

The optimal signal for the desired down-regulation of matrix metalloproteinase (MMP) gene regulation—including genes for MMP-1, MMP-3 and MMP-13, among others—was found systematically as follows. An electrical signal known to decrease (or even just suspected to decrease) cellular production of MMP is taken as the starting signal for determining the specific signal for generating the field for the gene expression (mRNA) of MMP. A dose-response curve is first performed by varying the duration of the signal while holding all the other signal characteristics constant (amplitude, duty cycle, frequency, and waveform) (FIGS. 1-3). This determines the optimal duration of the starting signal for the gene expression of MMP. A second dose-response curve is then performed, this time varying the duty cycle from 100% (constant) to 8.3% or less while holding the amplitude and other signal characteristics constant (FIGS. 4-6). A dose-response is repeated a third time (varying amplitude), a fourth time (varying frequency), and a fifth time (varying waveform)—each time keeping the other signal characteristics constant. By this method an optimal signal is determined for producing the greatest decrease in the gene expression of the various MMPs.

Protein expression may be determined by any method known in the art, such as real-time quantitative RT-PCR, Northern analysis, immunoassays, direct biochemical analysis, and the like.

Metalloproteinase Production by Articular Chondrocytes

Articular chondrocytes were exposed to a capacitively coupled electric field of 20 mV/cm at 60 kHz. The results are illustrated in FIGS. 1-6.

FIG. 1 is a graphic representation of MMP-1 mRNA expression when articulate cartilage chondrocytes are exposed to a 20 mV/cm capacitively coupled electric field for various time durations in the presence of interleukin (IL-1β). As indicated, the minimum MMP-1 expression occurred with a signal duration of 30 minutes. Maximum expression of MMP-1 mRNA occurred in the presence of IL-1β when no electricity was used.

FIG. 2 is a graphic representation of MMP-3 mRNA expression when articular cartilage chondrocytes are exposed to a 20 mV/cm capacitively coupled electric field for various time durations in the presence of IL-1β. As indicated, the minimum MMP-3 production occurred with signal durations of 30 minutes and 6 hours. Maximum expression of MMP-3 mRNA occurred in the presence of IL-1β when no electricity was used.

FIG. 3 is a graphic representation of MMP-13 mRNA expression when articulate cartilage chondrocytes are exposed to a 20 mV/cm capacitively coupled electric field for various time durations in the presence of IL-1β. As indicated, the minimum MMP-13 expression occurred with signal durations of 30 minutes and 24 hours. Maximum expression of MMP mRNA occurred in the presence of IL-1β when no electricity was used.

FIG. 4 is a graphic representation of MMP mRNA expression when articular cartilage chondrocytes are exposed to a 20 mV/cm capacitively coupled electric field of different duty cycles in the presence of IL-1β. As indicated, the minimum expression of MMP-1 mRNA occurred with a 100% duty cycle signal. Maximum expression of MMP-1 mRNA occurred in the presence of IL-1β when no electricity was used.

FIG. 5 is a graphic representation of MMP-3 mRNA expression when articular cartilage chondrocytes are exposed to a 20 mV/cm capacitively coupled electric field of different duty cycles in the presence of IL-1β. As indicated, minimum expressions occurred with 100% and 8.3% duty cycles. Maximum expression of MMP-3 mRNA occurred in the presence of IL-1β when no electricity was used.

FIG. 6 is a graphic representation of MMP-13 mRNA expression when articular cartilage chondrocytes are exposed to a 20 mV/cm capacitively coupled electric field of different duty cycles in the presence of IL-1β. As indicated, minimum expressions occurred with duty cycles of 100% and 50%. Maximum expression of MMP-13 mRNA occurred in the presence of IL-1β when no electricity was used.

As noted above, FIG. 7 illustrates a device 10 in accordance with the present invention that is used to treat a patient with osteoarthritis of the knee. As illustrated, two circular, soft conductive, self-adherent electrodes 12 are placed on the skin on either side of the knee at the level of the joint line. The electrodes 12 are attached to a power unit 14 that has a VELCRO® patch 16 on the reverse side such that the power unit 14 can be attached to a VELCRO® strap (not shown) fitted around the calf, thigh or waist. The electrodes 12 may be placed on the skin before the patient goes to bed each evening or any other convenient time. Of course, other suitable types of electrodes 12 or coils (for inductive coupling) may also be used.

The power unit 14 is preferably small (e.g., 6-8 ounces) and powered by a standard 9-volt battery to emit a 5 V peak-to-peak, 6-10 mA, 20 mV/cm, 60 kHz sine wave signal to the electrodes 12 placed on the skin. When this signal is provided approximately 30 minutes per day with the proper duty cycle (100% ), it has been shown to significantly down-regulate genes encoding matrix metalloproteinases. This treatment should prevent or minimize further articular cartilage deterioration as well as to heal articular cartilage that already is damaged or degenerated. This treatment should also prevent or minimize tumor metastasis.

The example described above demonstrates that the expression of MMP-1, MMP-3 and MMP-13 genes may be significantly down-regulated to decrease the production of the enzymes which destroy articular cartilage so as to treat arthritis (both osteoarthritis and rheumatoid arthritis), cartilage injury, and cartilage defects. Proteoglycan, along with type II collagen, are the main organic constituents of articular cartilage which are damaged, degraded and/or destroyed early in the development of arthritis by metalloproteinases. The present invention clearly shows that the optimal electric field described in the example can very significantly down-regulate MMP-1, MMP-3 and MMP-13 mRNA and, hence, decrease cartilage matrix destruction, even in the presence of IL-1β. Those skilled in the art will appreciate that an appropriate electric field, as described herein with capacitive coupling, is also equally effective with inductive coupling and all electromagnetic systems that produce equivalent, or nearly equivalent, electric field characteristics. Those skilled in the art will also appreciate that more unique signal characteristics may be discovered through more experimentation with more data points (e.g., a 100±3% duty cycle for 30±3 min), but such relatively minor variations in each of the signal characteristics are believed to be within the level of those skilled in the art given the teachings herein.

Those skilled in the art will also appreciate that numerous other modifications to the invention are possible within the scope of the invention. For example, the optimal field described herein can be applied to any joint via two or more appropriate surface electrodes, in pairs or strips, incorporated in garments, braces, wraps, or casts, and delivered by means of capacitive coupling. Also, the optimal field described here can be applied to any joint via coil(s) or solenoid incorporated into garments, braces, wraps, or casts, and delivered by means of inductive coupling. Accordingly, the scope of the invention is not intended to be limited to the preferred embodiment described above, but only by the appended claims

What is claimed is:

1. A method of down-regulating the gene expression of matrix metalloproteinases in target tissue, comprising the steps of:
    generating at least one specific and selective signal having a frequency of approximately 60 kHz that when applied to a field generating device operatively disposed with respect to said target tissue causes the generation of an electric field having an amplitude of about 10-20 mV/cm in the target tissue that is specific and selective for the down-regulation of the gene expression of matrix metalloproteinase in said target tissue as measured by mRNA when said electric field is applied to the target tissue containing said matrix metalloproteinase; and
    exposing the target tissue to the specific and selective electric field generated by said field generating device upon application of said at least one specific and selective signal thereto for a predetermined duration of time from approximately ½ hour to 24 hours per 24 hour period at a predetermined duty cycle from approximately 8.3% to 100% so as to selectively down-regulate the gene expression of the matrix metalloproteinase in said target tissue as measured by mRNA.

2. The method of claim 1 wherein the generating step comprises the step of selectively varying the amplitude, duration, duty cycle, frequency, and waveform of the specific and selective signal until the gene expression of matrix metalloproteinase in said target tissue as a result of exposure to the resultant specific and selective electric field as measured by mRNA in the target tissue is substantially reduced.

3. The method of claim 1 wherein said generating step comprises the step of exposing an articular cartilage chondrocyte to the specific and selective electric field for a duration of approximately 30 minutes every 24 hours.

4. The method of claim 1 wherein said generating step comprises the step of generating an electric signal having a sine wave configuration and a duty cycle of approximately 100%, where the resultant specific and selective electric field in the target tissue has an amplitude of approximately 20 mV/cm.

5. The method of claim 1 wherein said generating step comprising the step of generating the specific and selective signal at a remote source and said exposing step comprises the step of applying the specific and selective electric field to the target tissue.

6. The method of claim 1 wherein the exposing step comprises the step of applying the specific and selective signal to an electrode or one or more coils located near the target tissue.

7. The method of claim 6 wherein the exposing step comprises the step of applying the specific and selective electric field in the target tissue generated by the field generating device upon application of said at least one specific and selective signal thereto to the target tissue through capacitive coupling or inductive coupling.

8. The method of claim 7 wherein when the specific and selective signal is applied to said electrodes the generates a capacitive coupling electric field, and when the specific and selective signal is applied to said one or more coils said one or more coils generate an electromagnetic field or a combined field 9. A method for (1) treating osteoarthritis, rheumatoid arthritis, cartilage injury, and/or cartilage defects, (2) providing an adjunct to other therapies including cell transplantation, tissue-engineered scaffolds, and/or growth factors, and/or (3) treating cartilage defects, comprising the steps of:
    generating at least one specific and selective signal having a frequency of approximately 60 kHz that when applied to a field generating device operatively disposed with respect to the target tissue causes the generation of an electric field having an amplitude of about 10-20 mV/cm in the target tissue that is specific and selective for the down-regulation of the gene expression of matrix metalloproteinase in said target tissue as measured by mRNA when said electric field is applied to the target tissue containing said matrix metalloproteinase; and
    exposing the target tissue to the specific and selective electric field generated by said field generating device upon application of said at least one specific and selective signal thereto for a predetermined duration of time from approximately ½ hour to 24 hours per 24 hour period at a predetermined duty cycle from approximately 8.3% to 100% so as to selectively down-regulate the gene expression of matrix metalloproteinase in said target tissue as measured by mRNA.

10. The method of claim 9 wherein the exposing step comprises the step of the capacitively coupling or inductively coupling the specific and selective electric field to the target tissue.

11. The method of claim 9 wherein the exposing step comprises the step of applying either an electromagnetic field or a combined field to the target tissue.

12. The method of claim 9 wherein the generating step comprises the step of generating an electric field signal having a sine wave configuration and a duty cycle of approximately 100% where the resultant specific and selective electric field has an amplitude of approximately 20 mV/cm in the target tissue.

13. The method of claim 9 wherein the exposing step comprises the step of applying the specific and selective electric field to the target tissue for a duration of approximately 30 minutes every 24 hours.

14. The method of claim 9 wherein the generating step comprises the steps of starting with an electric signal that when applied to said field generating device generates an electric field that is known or thought to be effective on living cells, performing a first dose-response curve on the duration of stimulation of the electric field to determine an optimal duration; performing a second dose-response curve on the amplitude of the applied electric signal using the optimal duration as previously found to determine an optimal amplitude; performing a third dose-response curve on the frequency of the applied electric signal keeping the optimal duration and optimal amplitude as previously found to determine an optimal frequency; performing a fourth dose-response curve varying the duty cycle of the applied electric signal and keeping the optimal duration, amplitude, and frequency as previously found to determine an optimal duty cycle, and keeping the optimal duration, amplitude, frequency and duty cycle while varying the waveform until an optimal waveform for the down-regulation of the gene expression of matrix metalloproteinase as measured by mRNA in the target tissue is found.

15. A device for the treatment of osteoarthritis, rheumatoid arthritis, cartilage injury, and/or cartilage defects, comprising a signal source that generates at least one specific and selective signal having a frequency of approximately 60 kHz and a field generating device connected to the signal source so as to receive said at least one specific and selective signal and that is operatively disposed with respect to the target tissue, said field generating device upon receipt of said at least one specific and selective signal causing the generation of an electric field having an amplitude of about 10-20 mV/cm in the target tissue that is specific and selective for the down-regulation of the gene expression of metalloproteinase in the target tissue as measured by mRNA, said signal source controlling and varying duration of time of application of said at least one specific and selective signal for a predetermined duration of time from approximately ½ hour to 24 hours per 24 hour period and controlling and varying the duty cycle of said at least one specific and selective signal applied to said field generating device from approximately 8.3% to 100% so as to selectively down-regulate gene expression of matrix metalloproteinase in the target tissue as measured by mRNA as a result of application of the specific and selective field.

16. The device of claim 15 further comprising a portable power unit that drives said signal source.

17. The device of claim 15 further comprising means for attaching the field generating device to a body of a patient in the vicinity of target tissue.

18. The device of claim 15 further comprising means for attaching the signal source to a body of a patient.

19. The device of claim 15 wherein the electric field generated by application of said at least one specific and selective signal to the field generating device is applied to target tissue via capacitive coupling or inductive coupling.

20. The device of claim 19 wherein the specific and selective signal has a sine wave configuration and a duty cycle of approximately 100%, where the resultant specific and selective electric field has an amplitude of about 20 mV/cm in the target tissue.

21. A method of (1) treating osteoarthritis, rheumatoid arthritis, cartilage injury, and/or cartilage defects, (2) providing an adjunct to the other therapies including cell transplantation, tissue-engineered scaffolds, or growth factors, and/or (3) treating cartilage defects, comprising the steps of exposing the target tissue to the specific and selective electric field generated by the device of claim 20 so as to down-regulate gene expression of metalloproteinase (as measured by mRNA) in the target tissue.

22. A method of determining a specific and selective electric signal that when applied to a field generating device causes the field generating device to generate an electric field in target tissue that down-regulates matrix metalloproteinase (s) in the target tissue, comprising the steps of starting with a starting electric signal with a signal shape and frequency that when applied to said field generating device causes said field generating device to generate an electric field that is known or thought to affect cellular production of matrix metalloproteinase, selectively varying a duration of application of said starting signal until a duration that provides a most significant decrease in production of matrix metalloproteinase is found, selectively varying an amplitude of the starting signal using an amplitude that provides a most significant decrease in production of matrix metalloproteinase is found, selectively varying a duty cycle of the starting signal until a duty cycle that provides a most significant decrease in production of matrix metalloproteinase is found, and selectively varying an on-off interval of the duty cycle of the starting signal until an on-off interval that provides a most significant decrease in production of matrix metalloproteinase is found.

23. The method of claim 22 comprising the further steps of selectively varying a frequency and waveform of said starting signal, keeping other signal characteristics constant, until a most significant decrease in production of matrix metalloproteinase as measured by mRNA is found.

24. The device of claim 15 wherein the field generating device comprises an electrode or one or more coils.

* * * * *